United States Patent [19]

Worrell et al.

[11] 3,974,214

[45] Aug. 10, 1976

[54] ISOPHTHALIC ACID MANUFACTURE

[75] Inventors: G. Richard Worrell, Media; Alan R. Hirsig, Wallingford; Henry R. Grane, Springfield, all of Pa.

[73] Assignee: Atlantic Richfield Company, Los Angeles, Calif.

[22] Filed: Feb. 27, 1974

[21] Appl. No.: 443,642

[52] U.S. Cl............................................. 260/524 R
[51] Int. Cl.$^2$......................................... C07C 51/33
[58] Field of Search................................ 260/524 R

[56] References Cited
UNITED STATES PATENTS

| | | | |
|---|---|---|---|
| 2,723,994 | 11/1955 | Haefele et al.................. | 260/524 R |
| 3,406,196 | 10/1968 | Lewis et al..................... | 260/524 R |
| 3,595,908 | 7/1971 | Lumbroso....................... | 260/524 R |
| 3,607,919 | 9/1971 | Barone............................ | 260/524 R |
| 3,626,001 | 12/1971 | Keith et al. .................... | 260/524 R |
| 3,686,293 | 8/1972 | Gualdi et al. ................... | 260/524 R |
| 3,703,547 | 11/1972 | Lugo et al....................... | 260/524 R |

FOREIGN PATENTS OR APPLICATIONS

| | | | |
|---|---|---|---|
| 908,736 | 10/1962 | United Kingdom............ | 260/524 R |
| 1,237,786 | 7/1971 | United Kingdom............... | 26/524 R |

*Primary Examiner*—Anton H. Sutto
*Attorney, Agent, or Firm*—John R. Ewbank

[57] ABSTRACT

The severity of oxidation conditions in each of two stages is regulated so that the concentration of metatoluic acid in the liquid does not exceed 2 weight per cent in the first stage and does not exceed 0.4 weight per cent in the second stage. Total impurities and intermediate aromatic oxidation products are thus sufficiently low that the particles of isophthalic acid which grow in the slurry of reaction mixture in acetic acid do not contain an excessive amount of impurities. The flow rates of feed, interstage slurry, and product slurry as expressed in mols of aromatic components per hour are approximately equalized and regulated as a part of the monitoring to assure compliance with such oxidation severity standards, both stages being in the 100°–130°C. range.

6 Claims, No Drawings

ISOPHTHALIC ACID MANUFACTURE

FIELD OF THE INVENTION

This invention relates to the manufacture of isophthalic acid continuously by two stage treatment of a slurry in an aqueous acetic acid solvent by oxidation of metaxylene using a cobalt catalyst and blowing an oxygen-containing gas through the slurry.

PRIOR ART

Loder 2,245,528 describes a continuous manufacture of phthalic acids in an acetic acid solvent at 187°–202°C. Using cobalt acetate catalyst, air oxidation, and fifty atmospheres pressure. At an earlier period, methods for oxidizing alkylated mononuclear aromatics to acids were grouped together, but as separate markets and purity specifications evolved for each compound, the technology for each acid tended to become more unique. Proposals for plants adapted for intermittent manufacture of any of a variety of acids have been rarer as the technology for each acid became more specialized.

Although many processes are appropriate for laboratory investigation of oxidizing hydrocarbons to aromatic acids, the competition amongst the methods used industrially has been much influenced by the availability and price of hydrocarbons meeting various purity standards and the potential market and price of acids meeting various purity standards. Solvent grades of xylene having more than about 80 percent metaxylene have sometimes been available at attractive prices, but metaxylene having a purity better than 99.5 percent has not been readily available. Isophthalic acid process designers have generally had to design their methods on the assumption that the feedstock would contain several times the proportion of impurities that might be expected in some of the more desirable feedstocks for a terephthalic acid plant.

At an earlier period, isophthalic acid having significant amounts of impurities was a relatively readily marketed material, but some customers have had need for isophthalic acid as free from impurities as demanded by some customers for terephthalic acid. Such trends have magnified the separateness of the terephthalic acid technology and isophthalic acid technology.

Research and development concerned with isophthalic acid are described in Keith et al 3,626,001; Keith et al 3,646,124; Ohlswager 3,655,033; and Trevillyan 3,673,154, all assigned to Atlantic Richfield Company, assignee herein.

Isophthalic acid having an acceptable whiteness can contain impurities which impart color to resins made from such isophthalic acid. The potentialities for expansion for some of the markets for isophthalic acid have been dependent upon satisfactory elimination of troublesome amounts of color-producing bodies. Some approaches to the solution of this problem have involved purification procedures by which only a relatively small yield of highly purified isophthalic acid was recovered from a crude material. There has been a long-standing demand for a process for preparing crude isophthalic acid having characteristics suitable for yielding a recrystallized isophthalic acid adequately free from color bodies, but previous literature has failed to teach a practical method for achieving such goal.

SUMMARY OF THE INVENTION

In accordance with the present invention, a chemical grade of metaxylene is oxidized in air under pressure in a solution of acetic acid to form a slurry of isophthalic acid and the flow rate, expressed as mols of aromatic acid per hour, is substantially equalized at a feed supply, interstage, and product withdrawal, there being two reactors, the ratio of volume and/or residence time for the first reactor to the second reactor being within a range from 0.5:1 to 10:1. The severity of the oxidation reaction is controlled by appropriate monitoring and regulation of aromatic flow rate and temperature, the temperature being maintained within a range from about 100° to about 130°C. Some of the supplemental controls for maintaining the desired severity include the regulation of the concentration of cobalt catalyst, regulation of the rate of injection of acetaldehyde accelerator for the reaction, regulation of flow rate of the oxygen containing gas, and regulation of the concentration of the oxygen in such gas stream. The product withdrawn from the second stage corresponds essentially to the average composition of the mixture in the second stage, and the interstage mixture corresponds essentially to the average composition of the first stage of the system.

In the development of the present invention, it was discovered that at the time when the concentration of isophthalic acid exceeds the solubility limit of the solvent at reaction conditions, the isophthalic acid particles or crystals that form contain components dissolved in the liquid portion. Some theories suggest that each of the two methyl groups can be oxidized successively through many stages, possibly comprising an alcohol, aldehyde, and acid stage, some of which may temporarily interact to form other intermediates, so that many intermediate compounds can be contemplated in the oxidation of metaxylene to isophthalic acid. Color body formation is attributable in part to reactions of aldehydes. Analysis and monitoring of the extremely low concentrations of all the aldehydes is both difficult and unreliable. Monitoring and measuring the concentration of metatoluic acid is surprisingly more manageable and provides a more reliable method for preventing excessive entrainment of aldehydes and/or other color-forming bodies in the crude crystals of isophthalic acid growing as entrained particles in the slurries in each reactor.

Single stage continuous oxidation of metaxylene, at any practical combination of operating conditions, fails to adequately decrease the concentration of color-forming bodies and/or metatoluic acid. If there are scores of stages, the continuous process closely resembles a batch operation. In the early stages of a many-stage operation, or part way through a batch operation, reaction intermediates and color-forming bodies would be coprecipitated with IPA. By having two continuous stages in which the residence time and/or volume of the second stage is within a range from about one-tenth to about twice that of the first stage, adequate oxidation is efficiently achieved in both stages, giving satisfactorily low co-precipitation of impurities and color-forming bodies.

The metatoluic acid concentration in the liquid portion of the slurry of a small sample of the interstage stream is monitored in accordance with the present invention, and the oxidation severity of the first reactor is regulated to maintain such metatoluic acid concentration less than 2 percent and desirably below 1 percent by weight. Similarly, the severity of oxidation in the second reactor is regulated so that the concentration of metatoluic acid in the liquid portion of the slurried product stream is less than 0.4 percent, desirably less than 0.1 percent by weight. Severity of oxidation is regulatable in accordance with the invention: by regulating temperature within the 100° to 130°C. range; and by regulating flow rate of moles of aromatic component per hour to maintain the unit molar ratio of acetic acid to metaxylene within a range from 5 to 30, desirably about 8 to 12, or, expressed as a weight percent, the metaxylene concentration in the total liquid feed to the first reactor is about 5 to 27 percent, desirably about 12 to 18 percent Supplemental optional variables for controlling severity of oxidation include: regulating pressure within the 10 to 500 psig range; regulating the concentration of oxygen in the gas stream; controlling the flow rate of the oxygen-containing gas; regulating the concentration of acetaldehyde accelerator; and regulating the concentration of cobalt catalyst per mol of aromatic component. The cobalt catalyst is desirably an activated cobalt ion in a higher oxidation stage, as taught by the prior art; and the co-oxidation of acetaldehyde promotes preservation of such activated ion.

DETAILED DESCRIPTION

There have been many descriptions of methods in which alkylated mononuclear aromatic hydrocarbons are dissolved in a solvent and subjected to oxidation with an oxygen containing gas in the presence of a catalyst. In the development of the present invention, the importance of certain features was established to provide the basis for the claimed subject matter. Achieving isophthalic acid suitable for use by resin manufacturers without troublesome amounts of color-forming bodies has been emphasized in the development of the present invention. Various engineering modifications were possible, and prior literature is relied upon for teachings of appropriate ranges for modifications which feature the present invention, but differ from the illustrative embodiments. The previously identified Atlantic Richfield patents on isophthalic acid manufacture provide a reiterated disclosure of isophthalic acid manufacture and supplemental disclosure of appropriate ranges of variables which are not stressed in the presently claimed subject matter. The appropriate engineering design for a particular plant is adapted to meet a variety of needs, including compliance with local governmental regulations, compliance with pollution standards, availability of equipment from closed-down units, and other factors remote from chemical analysis.

A generic description of a two stage method of isophthalic acid manufacture is helpful in understanding the present invention. In a single stage system, either continuous or batch operation is appropriate. In a twenty stage system, the multiplicity of stages imparts to the continuous system some of the features normally associated with batch conversion. In a two stage continuous method, there are two reactors, each containing a significant volume of reaction mixture; and there are supply lines to the first reactor, interstage transfer lines, and product withdrawal lines from the second reactor. The stream of solution of crude product from the second reactor is directed to a product recovery system, in which the isophthalic acid is separated from the mother liquor. The water content of the mother liquor is reduced to permit the recycling of a dried mother liquor as the principal solvent for the system.

The proportion distribution of the average residence times of the aromatic components in each of the two reactors is proportional to the volume of liquid in the two reactors. The total residence time can be increased or decreased by adjusting the moles per hour flow rate of the aromatic components through the system, there being substantially the same flow rate for the supply to the first reactor, withdrawal of product stream, and interstage stream. The moles of water and acetic acid in the product differ from the moles in the recycled solvent, and other adjustments must be made to cope with differences in temperature, density, and related variables when regulating volume flow rate of reaction mixture.

Any such continuous two stage method for isophthalic acid production can be clarified and analyzed by consideration of the incremental changes in the composition of the supply streams, interstage stream, and product stream. Because supply lines and withdrawal lines are at different zones of a reactor, some concentration gradients exist within each reactor, but problems attributable to concentration gradient are minimized by using circulating pumps or agitators to maintain approximate uniformity of the reaction mixture within each reactor.

The oxidation of acetaldehyde to acetic acid serves to promote the activity of the oxidized cobalt ion which serves as a catalyst. In the present method, acetaldehyde is fed not merely to the first reactor, but also to the second reactor. Such acetaldehyde is designated as an accelerator or promoter because it enhances the catalytic oxidation to isophthalic acid. The present invention achieves such nearly stoichiometric conversion to crude isophthalic acid that the small conversion to carbon dioxide does not require detailed attention.

The method of making isophthalic acid can be generally described as requiring the use of a first reactor containing a reaction mixture to which is supplied a recycled dried mother liquor containing acetic acid, a small amount of water, the cobalt acetate catalyst, and dissolved recycled aromatic components. A variety of intermediate oxidation products can exist in a system in which metaxylene is being oxidized to isophthalic acid. However, metatoluic acid is the intermediate compound having a stability such that its concentration is more readily measurable than that of other intermediate oxidation products. Accordingly, the composition of the recycled mother liquor can be sufficiently clarified by referring to concentrations of acetic acid, water, cobalt catalyst, dissolved isophthalic acid, and dissolved metatoluic acid. The hydrocarbon feed, that is, a chemical grade of metaxylene, is pumped at a controlled rate into the first reactor, desirably after dilution in the recycled mother liquor. The acetaldehyde is also pumped into the first reactor at a controlled rate. The interstage stream is pumped from the first reactor to the second reactor at a controlled rate and the clarification of its composition indicates the extent of the reaction conducted in the first reactor. Acetaldehyde is fed to the second reactor in which the conversion to isophthalic acid is substantially completed. The crude product stream contains not only the acetic acid from the recycled mother liquor but also the acetic acid resulting from the oxidation of the acetaldehyde injected into the first reactor and the acetaldehyde injected into the second reactor. The product stream contains water, not merely from the recycled mother liquor, but also the water produced by the oxidation of the metaxylene to isophthalic acid. The product stream contains dissolved isophthalic acid and dissolved metatoluic acid in addition to the suspended particles of isophthalic acid product derived from the metaxylene feed.

Most of the conversion of the metaxylene to isophthalic acid occurs in the first reactor, so that the crystallization of the isophthalic acid and the growth of the particles of isophthalic acid occurs in the reaction mixture containing all of the intermediate oxidation products. Although the average residence time of the aromatic components in the first reactor is desirably about 4 hours (and within a range from about 1 to 10 hours in appropriate modifications), there is a reason for believing that a significant portion of the metaxylene molecules are oxidized to isophthalic acid in a much shorter time and that the prolonged residence time in the first reactor is for assuring a significant clean-up of the system for converting a high proportion of the metatoluic acid to isophthalic acid in the first reactor.

Particular attention is directed to the feature of analyzing a sample of filtered liquid derived from the interstage stream. The solids of the slurry are removed (e.g., centrifuge, filtration, etc.) to provide such liquid. According to the present invention, the first reactor is regulated to make sure that such liquid contains less than 2 percent by weight of metatoluic acid (sometimes abbreviated as MTA). By monitoring the concentration of the metatoluic acid in such liquid portion of the interstage and regulating the severity of the oxidation in the first reactor so that the concentration of metatoluic acid in the liquid portion of such interstage stream is less than 2 percent, many problems of purification of the isophthalic acid in subsequent steps of manufacture are significantly simplified. It is believed that some of the aldehydes which are intermediate oxidation products are capable of forming color bodies in resins derived from isophthalic acid. The concentration of aldehydes and/or other color forming intermediate oxidation products has been found to be generally proportional to the concentration of the metatoluic acid and if the concentration of aldehydes and/or other intermediate oxidation products is excessively high, then troublesome amounts of such intermediate oxidation product are entrained in the isophthalic acid particles formed in the slurry in the first reactor, thereby making it difficult to avoid the presence of troublesome color bodies in the resins made from purified isophthalic acid.

In the second reactor, a relatively high severity of oxidation is necessary for converting relatively low concentrations of metatoluic acid and color-causing intermediates to isophthalic acid. Such high severity of oxidation can be obtained using any of a variety of techniques, including injection of relatively high proportions of acetaldehyde per mol of metatoluic acid. Because the product stream from the second reactor is a slurry of isophthalic acid (sometimes abbreviated as IPA) particles representing an approximately stoichiometric conversion of the metaxylene feed, the process for purification of isophthalic acid and the recovery of the isophthalic acid from the crude product stream are simplified. Significant amounts of gaseous oxygen, although present in the two reactors, are absent from the purification steps. Aldehydes present in the purification steps can undergo reactions, including condensation to color-forming bodies, thus leading to the requirement for less than 0.4 percent MTA in the liquid portion of the crude product stream.

The nature of the invention is further clarified by reference to a plurality of illustrative examples.

EXAMPLE I

A stream of dried, recycled mother liquor containing acetic acid, water, cobalt catalyst, dissolved isophthalic acid (IPA), and dissolved metatoluic acid (MTA) is recycled to the first reactor at a rate of about 6297 grams per hour. Such recycled dried mother liquor consists essentially of 6,000 grams of acetic acid (100 mols), 108 grams of water (6 mols), 59 grams of cobalt ion catalyst (1 mol), 116 grams of IPA (0.7 mol), and 14 grams of MTA (0.1 mol). The feed rate per hour of the metaxylene is 1060 grams (10 mols) and the acetaldehyde promoter is supplied at a rate of 176 grams (4 mols) per hour. The average residence time in the first reactor is about 5 hours so that the mixture in the first reactor can be thought of consisting of essentially a composition corresponding to the 5 hour flow of the interstage stream.

If the metaxylene/acetic acid unit mol ratio is about 10, then most of the xylene is converted to isophthalic acid in the first reactor, such conversion to IPA being of the magnitude of from about 90 percent to 95 percent. The extent of conversion is not the controlling factor in regard to the overall attractiveness of the process, inasmuch as it is the concentration of intermediate oxidation products in the liquid portion of the first reactor which affects the amount of such intermediate oxidation product entrained in the crystals of isophthalic acid which grow in the agitated slurry in the first reactor. The innterstage stream has hourly flow rates corresponding to 9.1 mols of IPA product and 0.7 mols of recycled IPA, or a total of 9.8 mols (1627 g) of IPA. The interstage stream hourly flow rates include 100 mols of recycled acetic acid and 4 mols of by-product acetic acid resulting from the oxidation of the acetaldehyde promoter, or a total of 104 mols (6240 g), and 6 mols of recycled water and 18.2 mols of by-product water or a total of 24.2 mols (436 g) of water, and 1.0 mol (59 g) of cobalt catalyst.

Particular attention is directed to the concentration of metatoluic acid in the interstage stream, inasmuch as such concentration is much less than the solubility limit of metatoluic acid in the solvent system at the conditions prevailing in the first reactor and/or reaction system, whereby there is little propensity for the metatoluic acid to be entrained in the solid particles of isophthalic acid. Since MTA and other aromatic intermediates form solid solutions (of limited solubility) with IPA, there is a propensity to co-precipitate.

The interstage stream has hourly flow rates corresponding to about 0.1 mol of recycled metatoluic acid and about 0.9 mol of metatoluic acid as an intermediate product or a total of 1 mol of MTA (136 g). The interstage stream flow rate is about 8498 g per hour, comprising about 1511 g of IPA slurried solids and about 6987 g of liquid. The first stage of oxidation brings about the approximately stoichiometric conversion of the metaxylene to metatoluic acid and a high degree of conversion of the metatoluic acid to isophthalic acid. The purpose of the second stage reactor is to provide the severity of conditions promoting the completion of the conversion to isophthalic acid in the absence of any feed stream of metaxylene. The residence time in the second reactor desirably is about 1 hour, and the volume of reaction mixture desirably is about 1/5 that of the volume in the first reactor. Thus, the reaction mixture volume ratios and residence time ratios are substantially the same.

In the second reactor, acetaldehyde promoter is supplied at a rate corresponding to 1.3 mols (57 g) per hour so that the promoter is supplied at a rate corresponding to about 13 mol percent of the xylene feed rate or about 145 mol percent of the metatoluic acid scheduled for oxidation to isophthalic acid. Such 145 mol percent promoter helps to provide a very high severity of oxidation conditions in the second reactor to assure an approximately stoichiometric conversion of the metaxylene to isophthalic acid in the two stage process.

Each reactor is maintained at 300 psig and at a temperature of 110°C. Remarkably high selectivity and remarkably low carbon dioxide generation are achieved because the reaction temperature is maintained below 130°C., such low temperature also helping to minimize formation of color bodies.

A portion of the reaction mixture is pumped from each reactor through its liquid-liquid heat exchanger and back into the reactor. Such liquid-liquid cooling of the reaction mixture also serves to agitate the contents of the reactor and to help maintain the particles of isophthalic acid in suspension in the slurry.

The reaction mixture is further agitated (thus, helping to keep the particles suspended in the slurry) by reason of the passage of bubbles of oxygen-containing gas upwardly through the reaction mixture. The gas stream also flows through a zone adapted to recover acetic acid from the effluent gas prior to venting of whatever portion of the cooled gas is not recirculated. Some of the cooling of the reactor is attributable to gasflow and cooling of the gas input and effluent. Air is ordinarily the source of oxygen, but a technical grade of oxygen can be mixed with carbon dioxide, nitrogen, or other diluent. It is generally advantageous to include recirculated gas in the diluent and to maintain the oxygen content below 20 percent in order to enhance the effectiveness of the gas circulation in cooling the reaction mixture to within the 100°–130°C. range.

Moreover, such dilution also decreases the likelihood of the existence of explosive mixtures. The use of pressures in the range from 10 pounds to 500 psig is for the purpose of providing an adequate partial pressure of oxygen while still avoiding the existence of readily flammable mixtures in the vapor space above the reaction mixture. The oxygen concentration of the gas supplied to each reactor is not more than 50 percent and the flow rates of the gas are regulated so that the oxygen concentration in the vapor space above the reaction mixture is desirably below about 8 percent oxygen. In this example the oxygen concentration is desirably about 10 percent in the gas supplied to each reactor.

A variety of poisons, such as orthophthalic acid can impair the activity of the cobalt acetate catalyst. The potential failure of the catalyst helps create a hazard of an absence of oxidation in the liquid and an oxygen concentration in the hot vapor above the liquid approximately equal to the oxygen concentration in the injected gas. Safety advantages are achieved by lowering the concentration of oxygen in the gas supplied to each reactor and increasing the total gas flow rate and total pressure so that the desired reaction rates are maintained with oxygen concentrations below the explosive limit even when the catalyst is completely poisoned or absent. In the first reactor, the gas flow rate is adjusted to provide at least 60 percent excess oxygen and the flow rate of oxygen containing gas to the second reactor is generally more than 100 percent in excess of that scheduled for consumption. Some of the cooling of the reaction mixture can be attributable to the injection of the oxygen containing gas at a relatively low temperature, such as ambient temperature, and the return of condensed acetic acid from the cooled vapor from the vapor zone above the reaction mixture.

The nature of the changes in the composition of the reaction mixture are clarified in Tables I through IV as follows:

Column headings:
A recycled dried mother liquor
B feed and promoter to first stage
C effluent from first stage (interstage)
D promoter to second stage
E effluent from second stage (crude product)

TABLE I

| | Moles/Moles Metaxylene/Hour | | | | |
|---|---|---|---|---|---|
| | A | B | C | D | E |
| acetic acid/xylene | 10 | | 10.4 | | 10.53 |
| water/xylene | 0.6 | | 2.4 | | 2.6 |
| catalyst/xylene | 0.1 | | 0.1 | | 0.1 |
| IPA/xylene | 0.07 | | 0.98 | | 1.07 |
| MTA/xylene | 0.01 | | 0.1 | | 0.01 |
| acetaldehyde/xylene | | 0.40 | | 0.13 | |
| xylene | | 1.00 | | | |

TABLE II

| | Moles per Hour | | | | |
|---|---|---|---|---|---|
| | A | B | C | D | E |
| Acetic acid | | | | | |
| recycle | 100.0 | | 100.0 | | 100.0 |
| by-product | | | 4 | | 5.3 |
| Water | | | | | |
| recycle | 6 | | 6 | | 6 |
| by-product | | | 18.2 | | 20.0 |
| Catalyst | 1.0 | | 1.0 | | 1.0 |
| IPA | | | | | |
| recycle | 0.7 | | 0.7 | | 0.7 |
| product | | | 9.1 | | 10.0 |
| MTA | | | | | |
| recycle | 0.1 | | 0.1 | | 0.1 |
| intermed | | | 0.9 | | |
| Acetaldehyde | | 4.0 | | 1.3 | |
| Xylene | | 10.0 | | | |
| Aromatics | 0.8 | | 10.8 | | 10.8 |

TABLE III

| | Grams/Hour | | | | |
|---|---|---|---|---|---|
| | A | B | C | D | E |
| Acetic Acid | 6000 | | 6240 | | 6318 |
| Water | 108 | | 436 | | 468 |
| Catalyst | 59 | | 59 | | 59 |
| IPA | 116 | | 1627 | | 1776 |
| MTA | 14 | | 136 | | 14 |
| Xylene | | 1060 | | | |
| Acetaldehyde | | 176 | | 57 | |
| TOTALS | 6297 | 1236 | 8498 | 57 | 8635 |
| | | 7533 | 8555 | | |
| Liquids | | | 6987 | | |
| Solids | | | 1511 | | |

TABLE IV

| | Per Cent by Weight/Hour | | | | |
|---|---|---|---|---|---|
| | A | B | C | D | E |
| Acetic acid | 79.6 | | 72.9 | | 73.1 |
| Water | 1.4 | | 5.1 | | 5.4 |
| Catalyst | 0.9 | | 0.7 | | 0.7 |
| IPA | 1.5 | | 19.0 | | 20.6 |
| MTA | 0.2 | | 1.6 | | 0.2 |
| Xylene | | 14.1 | | | |
| Acetaldehyde | | 2.3 | | 0.7 | |
| | | 100.00 | | 100.00 | |

The interstage stream C can be separated to provide 1511 g/hr of IPA solids and 6987 g/hr of liquid, so that the concentration of MTA in such liquid is 1.9 percent, well below the 4.0 percent maximum, but above the 1.6 percent MTA in the feed to the second reactor (Table IV). The data of Tables I–IV show that the two stage oxidation permits maintenance of the metatoluic acid concentration below 2 percent of the liquid portion of the first reactor and below 0.4 percent of the liquid in the second reactor.

The slurry of IPA in the product stream can be employed for the preparation of crystallized IPA suitable for polyester resin manufacture without development of troublesome coloration in the resins derived from the IPA. The crude product is transferred from the second reactor through a liquid-liquid heat exchanger to cool the stream from 110°C. to about 50°C. and directed to a separation zone having a centrifuge, filter press, or other suitable system for preparing a crude filter cake. Such filter cake is washed with acetic acid and then slurried in the solvent employed for recrystallization, desirably aqueous acetic acid. The slurry is heated to a pressure and temperature at which all of the slurry is dissolved in the hot acetic acid. Purified IPA is crystallized from this hot solution of acetic acid by two stages of evaporative crystallization in which the pressure and temperature are so controlled that a significant portion of the acetic acid is evaporated or distilled while precipitating a slurry of purified IPA crystals. All impurities remain dissolved in the recrystallization mother liquor and are separately processed so that the recrystallized IPA product may have the desired purity. The recrystallized IPA is subjected to drying to remove residual acetic acid and to provide a white powdery isophthalic acid having a purity acceptable for end use in resins free from troublesome amounts of color bodies.

EXAMPLE II

Isophthalic acid is manufactured by a method resembling Example I except that the flow rates of the gas streams through the two reactors are increased sufficiently to adequately cool the reaction mixture to 110°C. without the use of liquid-liquid heat exchangers while curtailing xylene flow rate by 40 percent and correspondingly adjusting the amount of promoter injection. The cooling capacity of the system is normally operated at a safe margin below maximum cooling capacity. The conversion to IPA in the first reactor is only about 60 percent, and the limitation of 2 percent MTA in the interstage liquid is still achieved.

EXAMPLE III

Isophthalic acid is made by a method resembling Example I, one of the exceptions being that each reactor is operated at a pressure of about 40 psig, whereby the circulating gas stream volatilizes larger amounts of acetic acid for cooling the reactor by reflux of the acetic acid at a temperature of about 127°C. The injection of acetaldehyde is increased 30 percent. The oxygen content of the oxygen containing gas to each reactor is increased to about 20 percent. The residence times are about 10 hours and 2 hours because of the limitations on the partial pressure of oxygen at the lower pressure. However, benefits accrue from the simplification of the cooling and the reduction in the pressure for the reactors.

EXAMPLE IV

Isophthalic acid is made by a method resembling Example I except that the second reactor is cooled by reflux while relying upon the liquid-liquid heat exchangers to cool the first reactor. Because the MTA concentration of the feed to the second reactor is less than 2 percent of the liquids, high severity oxidation conditions can be maintained while operating at 40 psig and reflux conditions. Both operating expense and capital expense are saved by such avoidance of liquid-liquid heat exchangers and high pressure reactor for the second stage.

EXAMPLE V

Isophthalic acid is prepared by a method resembling Example I except that the first reactor is operated at reflux at about 40 psig and the second reactor employs a pressure of about 300 psig and liquid-liquid heat exchangers for cooling the system. High severity oxidation conditions are maintained in the relatively small second reaction for assuring adequate clean-up for minimizing MTA concentration in the product stream while achieving the advantages of low capital costs for the first stage.

EXAMPLE VI

By a series of tests, it is established that there should be appropriate limits for the ranges to be employed while keeping the MTA concentration in the effluent from the first reactor below 2 percent and the MTA concentration in the liquid effluent from the second reactor below the 0.4 percent. The most significant limitations are set forth in Table V as molar ratios. There are many blanks in Table V because little importance is attached to some of the conditions provided the significant controls are maintained.

A general perspective on the possible variations in the two stage process while maintaining the important limits of less than 2 percent MTA in the liquid effluent from the first reactor and less than 0.4 percent MTA in the liquid effluent from the second reactor are set forth in Table VI, some of the data of which represents engineering estimates as distinguished from experimentally established criteria.

TABLE V

| | Appropriate Ranges - Molar Ratios | | | | |
|---|---|---|---|---|---|
| | A | B | C | D | E |
| Acetic acid/water | 2–1000 | | | | |
| Solvent/Xylene | | | 5–30 | | |
| Co/aromatic compounds | 0.05–5.0 | | | | |
| Acetaldehyde/xylene | | | | 0.05–1.0 | 0.05–1.0 |
| Acetaldehyde/ | | | | | |

TABLE V-continued

| | Appropriate Ranges - Molar Ratios | | | | |
|---|---|---|---|---|---|
| | A | B | C | D | E |
| metatoluic acid | | | | 0.5–15 | |

TABLE VI

| | Appropriate Ranges Per Cent by Weight | | | | |
|---|---|---|---|---|---|
| | A | B | C | D | E |
| Acetic acid | 80–99.3 | | 70–95 | | 70–95 |
| Water | 0.1–4.0 | | 3–9 | | 3–9 |
| Cobalt catalyst | 0.4–4.0 | | 0.3–3.5 | | 0.3–3.5 |
| Isophthalic acid | 0.1–3.0 | | 3–25 | | 3–25 |
| Metatoluic acid | 0.1–3.0 | | 0.2–2.0 | | 0.1–0.3 |
| Xylene | | 5–30 | | | |
| Acetaldehyde | | 0.1–10 | | 0.1–10 | |

By a series of tests it is shown that when large amounts of MTA are present in the liquids in either reactor, the IPA which has been recrystallized from acetic acid is unsatisfactory for resin production because of color-forming bodies. Further purification of the IPA by recrystallization from water, although sometimes effective in separating an impure IPA from a purified IPA having a low concentration of color-forming bodies, is an unsatisfactory route to the desired product because it involves pollution problems, expense, and equipment problems which are not readily managed.

EXAMPLE VII

Isophthalic acid is made following the general pattern of Example I and in an apparatus providing for the recirculation of dried mother liquor at a rate of about 173 tons per day, xylene feed of about 30 tons per day, and acetaldehyde injection at the rate of about 5 tons per day. Because the oxidation temperature is maintained below 130° and within the the range from 100° to 130°, and because the MTA concentration in the effluent from the first reactor is maintained below 2 percent and because the MTA concentration in the liquid product stream is maintained below 0.4 percent, the dried recrystallized IPA is suitable for the manufacture of polyester resins without development of objectionable color.

Various modifications of the invention are possible, so that the examples should be deemed to be merely illustrative embodiments of the invention, which is defined in the appended claims.

We claim:

1. A continuous method of manufacturing isophthalic acid which comprises the steps of:
   a. feeding to a first reactor system the combination of metaxylene and acetaldehyde, said first reactor system consisting essentially of a mixture of said metaxylene, acetaldehyde, a principal amount of aqueous acetic acid, isophthalic acid in both slurried and dissolved form, cobalt catalyst, and intermediate oxidation components and directing oxygen containing gas through said mixture, the components having an aromatic structure being designed as aromatic components, the unit molar ratio of acetic acid to aromatic components being maintained within a range from about 5 to about 30, the unit molar ratio of cobalt catalyst to aromatic components being maintained within a range from about 0.05 to about 5, and said first reactor being maintained at a pressure within a range from about 10 to 500 psig;
   b. withdrawing from said first reactor system an interstage stream of said mixture for transfer to a second reactor system, said mixture consisting of solids suspended in a liquid portion;
   c. feeding acetaldehyde to a second reactor system consisting essentially of a mixture of said acetaldehyde, aqueous acetic acid, isophthalic acid, cobalt catalyst, and intermediate oxidation products, said second reactor system containing from about one-tenth to about twice the volume of reaction mixture as said first reactor system and directing oxygen containing gas through said mixture for maintaining the second reactor system at a pressure within the range from about 10 to 500 psig;
   d. withdrawing from said second reactor system a stream of said mixture for transfer to a system for recovery of isophthalic acid, the flow rate of such withdrawn product stream, expressed as moles of aromatic components per hour, being substantially the same as the flow rate to said second reactor;
   e. regulating flow rates and volume of mixture in the first reactor to maintain average residence time of aromatic components in the first reactor within a range from about 1 hour to 10 hours, the average residence time in the second reactor being from one-fifth hour to 10 hours, the average residence time in the second reactor being from one-fifth hour to 10 hours, the total residence time being within the range from about 1.2 to about 20 hours;
   f. controlling the temperature of each reactor system to be within the range from about 100°C. to 130°C.;
   g. regulating the temperature to each reactor system and regulating the aromatic component flow rate to maintain in the first reactor a large molar ratio of isophthalic acid to metatoluic acid and to maintain the concentration of metatoluic acid below 2 weight percent of the liquid portion of the stream withdrawn from the first reactor system and to maintain in the second reactor a large molar ratio of iosphthalic acid to metatoluic acid and to maintain in the liquid portion of the stream withdrawn from the second reactor a concentration of metatoluic acid below 0.4 weight percent, whereby purified isophthalic acid adequately free from color-forming bodies can be withdrawn from said isophthalic acid recovery system.

2. The method of claim 1 in which the isophthalic acid recovery system comprises a zone in which a filter cake of crude isophthalic acid is separated from the withdrawn product stream, said filter cake is dissolved in a predominantly organic solvent, and purified isophthalic acid is recrystallized from said solution of the crude isophthalic acid in said solvent.

3. The method of claim 1 in which liquid-liquid heat exchangers are employed to cool the mixtures in each of said reactor systems.

4. The method of claim 1 in which continuous operation at said 2 percent and 0.4 percent metatoluic acid standards is maintained by monitoring and regulating said flow rates and said reactor temperatures and by supplemental regulation of the unit mol ratio of aromatic components to cobalt catalyst and the unit mol ratio of aromatic components to acetaldehyde.

5. The method of claim 1 in which the unit molar ratio of acetic acid to aromatic components is maintained within a range from about 8 to about 12.

6. The method of claim 1 in which the amount of acetaldehyde fed to the second reactor is within the range from 0.5 to 15 mols per mol of metatoluic acid in the interstage stream.

* * * * *

UNITED STATES PATENT OFFICE
CERTIFICATE OF CORRECTION

PATENT NO. : 3,974,214
DATED : August 10, 1976
INVENTOR(S) : G. Richard Worrell, Alan R. Hirsig & Henry R. Grane It is certified that error appears in the above-identified patent and that said Letters Patent are hereby corrected as shown below:

Column 11, lines 61-62 - In Claim 1 the word "designed" should be deleted and the word "designated" substituted in its place.

Signed and Sealed this

Twenty-sixth Day of October 1976

[SEAL]

Attest:

RUTH C. MASON
Attesting Officer

C. MARSHALL DANN
Commissioner of Patents and Trademarks